United States Patent [19]

Burger

[11] Patent Number: 5,753,180
[45] Date of Patent: May 19, 1998

[54] METHOD FOR INHIBITING MICROBIALLY INFLUENCED CORROSION

[75] Inventor: Edward Daniel Burger, Plano, Tex.

[73] Assignee: Bio-Technical Resources, Manitowoc, Wis.

[21] Appl. No.: 695,354

[22] Filed: Aug. 9, 1996

Related U.S. Application Data

[63] Continuation-in-part of Ser. No. 423,663, Apr. 17, 1995.

[51] Int. Cl.$^6$ .............................. C23F 11/00; C23F 11/06
[52] U.S. Cl. ................... 422/7; 422/13; 422/14; 435/262; 435/266; 435/281; 134/42
[58] Field of Search ...................... 422/7, 13, 14; 435/262, 243, 260, 281; 210/696, 698; 134/42; 106/14.41, 14.42; 252/315.01, 315.2; 427/214

[56] References Cited

U.S. PATENT DOCUMENTS

| | | | |
|---|---|---|---|
| 4,561,981 | 12/1985 | Characklis | 210/696 |
| 5,385,842 | 1/1995 | Weimer et al. | 435/262 |
| 5,500,368 | 3/1996 | Tatnall | 435/262 |

FOREIGN PATENT DOCUMENTS

| | | |
|---|---|---|
| 0 591 000 A1 | 6/1994 | European Pat. Off. |
| WO 94/08738 | 4/1994 | WIPO |

OTHER PUBLICATIONS

Perkins & Euchner, Safe Purging of Natural Gas Pipelines, *SPE Production Engineering*, 663–668, Nov. 1988.

Costerton & Lashen, Influence of Biofilm on Efficacy of Biocides on Corrosion-Causing Bacteria, *National Association of Corrosion Engineers*, 13–17, Feb. 1984.

Blenkinsopp et al., Electrical Enhancement of Biocide Efficacy against Pseudomonas aeruginosa Biofilms, *Applied and Environmental Microbiology*, 58, No. 11, 3770–3773, Nov. 1992.

*Primary Examiner*—Nina Bhat

[57] ABSTRACT

A non-biocidal method for inhibiting microbially influenced corrosion of susceptible metal surfaces having an anaerobic biofilm containing active sulfate-reducing bacteria comprising contacting the biofilm with a liquid dispersion of anthraquinone compound.

12 Claims, 2 Drawing Sheets

METHOD FOR INHIBITING MICROBIALLY INFLUENCED CORROSION

RELATED APPLICATIONS

This application is a continuation-in-part of copending U.S. application Ser. No. 08/423,663, filed Apr. 17, 1995.

FIELD OF INVENTION

The invention is directed to a method for inhibiting microbially influenced corrosion. In particular, it is directed to a method for inhibiting microbially influenced corrosion of susceptible metals in contact with aqueous liquid systems.

BACKGROUND OF THE INVENTION

In the oil industry, uncontrolled microbial growth and activity can create severe operational, environmental, and human safety problems. Problems caused or intensified by microbial growth and activity include corrosion, solids production, and hydrogen sulfide ($H_2S$) generation.

The microorganisms primarily responsible for corrosion in an anaerobic environment within the oil industry are sulfate-reducing bacteria. These organisms are ubiquitous and can grow in almost any environment. They are routinely found in waters associated with oil production systems and can be found in virtually all industrial aqueous processes, including cooling water systems, paper-making systems, and petroleum refining.

Requirements for sulfate-reducing bacteria activity and growth include an anaerobic (oxygen-free) aqueous solution containing adequate nutrients, an electron donor, and electron acceptor. A typical electron acceptor is sulfate, which produces $H_2S$ upon reduction. A typical electron donor is a volatile fatty acid (e.g., lactic, acetic, or propionic acids), although hydrogen can also function as the electron donor. Conditions in an oil reservoir subject to seawater flooding are excellent for establishing sulfate-reducing bacteria activity. Seawater contains a significant concentration of sulfate, while connate, or indigenous formation, water contains volatile fatty acids and other required trace nutrients (e.g., nitrogen and phosphorus). Mixtures of the two waters in a reservoir provide all of the essential conditions for sulfate-reducing bacteria activity. This condition will result in sulfide generation within the reservoir, which is referred to as reservoir souring.

Hydrogen sulfide is corrosive and reacts with metal surfaces to form insoluble iron sulfide corrosion products. In addition, $H_2S$ partitions into the water, oil, and natural gas phases of produced fluids and creates a number of problems. For instance, oil and gas, which contain high levels of $H_2S$, have a lower commercial value than low sulfide oil and gas. Removing biogenic $H_2S$ from sour oil and gas increases the cost of these products. Hydrogen sulfide is an extremely toxic gas and is immediately lethal to humans at even small concentrations. Thus, its presence in the oil field poses a threat to worker safety. The discharge of produced waters containing high levels of $H_2S$ into aquatic or marine environments is hazardous because $H_2S$ reacts with oxygen and lowers the dissolved oxygen levels in the water.

Waters produced from a reservoir in association with oil production, especially those resulting from a seawater flood, will typically contain sulfate-reducing bacteria and required nutrients. Conditions in surface facilities (e.g., pipelines, vessels, tanks) are usually quite favorable for sulfate-reducing bacteria activity. Furthermore, they are capable of activity and growth in a wide range of temperatures found in the oil field. Reduced temperatures in surface facilities many times enhance microbial growth as compared to elevated temperatures within the reservoir. Oil production operations favor the growth of anaerobic sulfate-reducing bacteria since those environments are usually kept oxygen-free to avoid oxidation corrosion of steel vessels, pipelines, and tanks. However, even if systems are aerobic, localized anaerobic conditions are maintained on the metallic surface (the substratum) beneath the biofilm due to oxygen consumption by aerobic bacteria.

Bacterial corrosion is actually caused by sessile anaerobic bacteria living under a thick biofilm composed of aerobic and facultative bacteria enmeshed in a fibrous anionic ion exchange resin that severely limits the penetration of charged molecules. (Costerton, J. W. and E. S. Lashen, "Influence of biofilm on efficacy of biocides on corrosion-causing bacteria," Materials Performance, 23, No. 2, p.13, 1984.) Waters used for cooling in heat exchangers are normally not deaerated, but sulfate-reducing bacteria growth flourishes on tube bundles unless extreme preventative measures are taken.

Sulfate-reducing bacteria activity in surface facilities is a source of $H_2S$ production, which causes corrosion, and results in the production of solid corrosion products, which may cause operational problems such as plugging of water-injection perforations in injection wells. (Produced waters acre frequently reinjected into the formation for secondary oil recovery purposes, or may be disposed of by injection into a different portion of the reservoir.) Inhibition of sulfate-reducing bacteria activity will reduce $H_2S$ production and will halt anaerobic corrosion of the steel surfaces, thereby reducing solids formation.

Corrosion (pitting) caused by sulfate-reducing bacteria frequently results in extensive damage. Pipe systems, tank bottoms, and other pieces of oil production equipment can rapidly fail if there are areas where microbial corrosion is occurring. If a failure occurs in a pipeline or oil storage tank bottom, the released oil can have serious environmental consequences. If a failure occurs in a high pressure water or gas line, the consequences may be worker injury or death. Any failure involves repair or replacement costs.

Potential methods for mitigating sulfate-reducing bacteria activity include: temperature control, metabolite removal, pH control, Eh control, radiation, filtration, salinity control, chemical control (e.g., oxidizers, biocides, acids, alkalis), solids control (e.g., pigging or scraping the internal pipeline), and bacteriological controls (e.g., bacteria phages, enzymes, parasitic bacteria, monoclonal antibodies, competitive microflora). Some of these methods will kill the sulfate-reducing bacteria, while others stress or disturb them sufficiently to inhibit their activity.

Most of the above methods are not practical for oil field implementation due to their cost or potential effect on the downstream processes. For example, treating of large quantities of water by heating to sterilization temperatures, by filtering out the microscopic bacteria, or by removing a nutrient (e.g., sulfate) is prohibitively expensive due to large equipment and energy requirements. Removal or the killing of bacteria from a process stream must be 100% effective or else exponential growth of surviving bacteria will recolonize downstream surfaces. In addition, all downstream surfaces must be sterilized (i.e., bacteria-free) prior to implementation of a sulfate-reducing bacteria mitigation process upstream or else sulfate-reducing bacteria growth will continue within the biofilm.

Two typical methods of controlling sulfate-reducing bacteria in oil field pipeline systems are pigging and biocide treatments. Pigging is required to remove or disrupt the biofilm on the pipe surface. Pigging can also remove many of the iron sulfide deposits which may be acting as cathodes to the corroding anodic areas. While pigging will be substantially effective where thick biofilms are present, thin biofilms and thin iron sulfide deposits are not appreciably affected by the scraping action of pigs. Subsequently, biocides and surfactant-biocide treatments are used extensively to control bacterial activity in oil field systems. Combination treatments in conjunction with pigging are more effective than the chemical treatments alone. However, treatments must be made routinely on a fixed schedule or else the bacteria population increases significantly and control becomes even more difficult. Monitoring the effectiveness of treatments must include the sessile bacteria, for the reason that the numbers of planktonic bacteria following a biocide treatment may have no correlation with the sessile bacteria involved with the corrosion process.

It has proved difficult to eradicate biofilms from pipelines because of their great resistance to bactericidal agents. The concentration of biocides required to kill bacteria in the sessile phase (in the biofilm) are often much higher than those required for bacteria in the planktonic or free-floating phase. (Blenkinsopp, S. A., Khoury, A. E. and Costerton, J. W., "Electrical enhancement of biocide efficacy against *pseudomonas aeriuginosa* biofilms," Applied and Environmental Microbiology, 58, No. 11, p. 3770, 1992.) This may be due to the role of the abundant exopolysaccharide matrix of the biofilm. It has been suggested that the diffusion resistance in the biofilm mode of growth can be overcome by the imposition of a relatively weak DC electric field so that the biofilm bacteria can readily be killed by concentrations of biocides only one to two times those necessary to kill planktonic cells of the same organism. While this new technology may be technically effective, it appears to be impractical to apply it in a commercial pipeline system.

SUMMARY OF THE INVENTION

In the broadest aspect, the invention is directed to a non-biocidal method for inhibiting microbially influenced corrosion of microbially influenced corrosion-susceptible metal surfaces having an anaerobic biofilm containing active sulfate-reducing bacteria comprising contacting the biofilm with a liquid solution of an alkali metal salt of anthrahydroquinone by which the anthrahydroquinone salt passes through the pores of the biofilm and is diffused within the biofilm to effect contact with the sulfate-reducing bacteria.

In a second aspect, the invention is directed to a method for inhibiting microbially influenced corrosion of pipelines constructed from susceptible metals through which liquids are transported in turbulent flow comprising introducing a liquid solution of an alkali metal salt of anthrahydroquinone into the flowing liquid as a plug, the volume of which is sufficient to provide contact with a given point within the pipe for at least one minute.

DETAILED DESCRIPTION

Biofilm

A biofilm is a heterogeneous accumulation of bacterial colonies attached to a substratum. Though characterized as a "biofilm," it is neither completely biological, nor is it continuous in the conventional sense of the word "film."

Recent studies indicate that a biofilm consists of discrete bacterial microcolonies immobilized on a substratum immersed in an aqueous medium, the microcolonies being separated by water channels through which convective flow can take place. The microbial cells are held together and held to the substratum surface by extra cellular polymeric substances. Within the context of the invention, the medium (also called "the substrate") is an anaerobic liquid and at least a significant portion of the bacteria in the biofilm are sulfate-reducing. However, the biofilm can contain other co-existing bacterial species. In addition, the biofilm can contain extraneous material such as exoenzymes, solutes and inorganic inclusions such as corrosion products, silt and clay particles.

Figure 1:
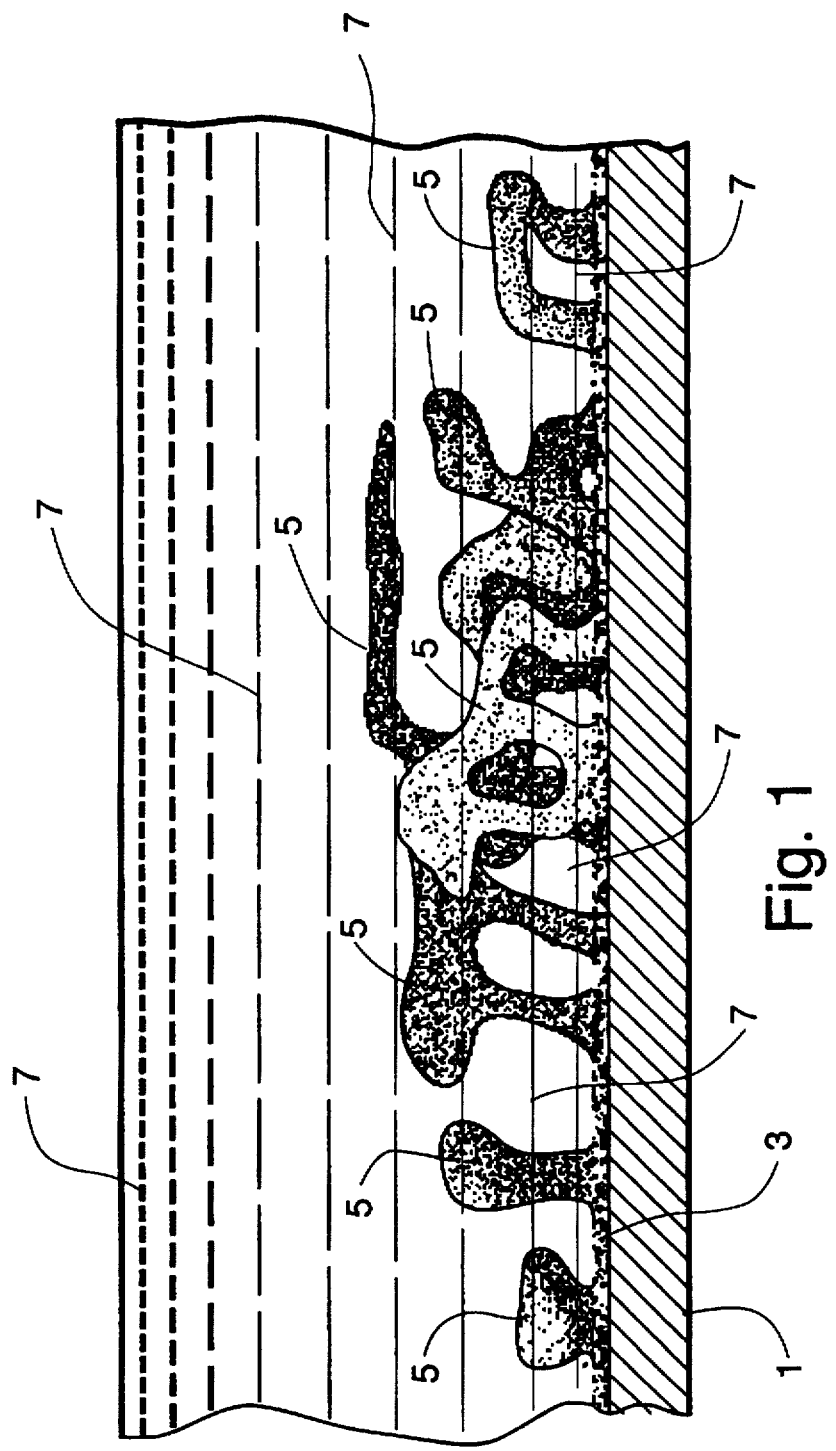
FIG. 1 is a schematic representation of a typical biofilm and FIG. 2 is a schematic representation of the valving involved in the use of pipeline scrapers (pigging)

FIG. 1 is a schematic representation of a biofilm which is attached to a metal substratum 1. As shown, a continuous thin layer of bacteria 3 is directly attached to the substratum 1. However, this layer 3 is not always continuous and its continuity does not enter into the efficacy of the invention in this environment. Attached to the thin bacterial layer 3, and/or directly to the substratum 1, as the case may be, is a series of bacterial cell clusters 5 having channels between them through which the aqueous medium 7 can flow. Because of the porosity of the bacterial cell clusters 5, the aqueous medium 7 and materials dispersed therein are able to enter the structure and contact bacteria within the structure.

Anthrahydroquinone Functionality and Applications

While biocides are aimed at killing sulfate-reducing bacteria, anthrahydroquinones inhibit their activity. Results from studies indicate that anthrahydroquinone blocks the production of adenosine triphosphate by sulfate-reducing bacteria, thereby removing the bacteria's ability to respire via sulfate reduction. Without sulfate reduction, $H_2S$ is not produced by the bacteria.

Biocides are very reactive, a property which is likely responsible for their limited effectiveness in penetrating the biofilms at low dosages. The extraordinary effectiveness of various forms of anthrahydroquinone lies in their non-reactivity. These products are transported into the biofilm, diffuse through the biofilm voids, and then diffuse or are randomly transported by Brownian motion into the bacterial microcolonies without reduction in concentration as a consequence of a reaction with biofilm constituents. These anthrahydroquinone materials are unaffected by other bacteria or the exopolysaccharide matrix present in the biofilm.

Even though solid particles of anthrahydroquinone are required to inhibit the sulfate-reducing bacteria activity, the anthrahydroquinone can be introduced into the anaerobic microbial environment as an ionic alkali metal salt in which the anthrahydroquinone is solubilized in an anaerobic solution with a pH greater than 12 and preferably greater than 13. The salt stays soluble if the pH of the solution remains above about 12; precipitation of solid anthrahydroquinone takes place as the pH is reduced below this value. In the soluble form, or with a slight amount of precipitated anthrahydroquinone (typically in colloidal form), anthrahydroquinone is either in ionic form or in the form of extremely small (submicron-sized) particles. The anthrahydroquinone ions or colloidal particles will then be able to move freely in the biofilm, thus contacting sulfate-reducing bacteria cells easily. Contact of anthrahydroquinone with the sulfate-reducing bacteria, and partitioning of the anthrahydroquinone into the cell membrane blocks the organism's adinosine triphosphate production. In addition, decreases in pH in the biofilm (due to acid production from other bacteria in the biofilm or due to a sweeping of lower pH fluid through the pipe) will precipitate more small anthrahydroquinone particles from the solution within the biofilm. This will expose the sulfate-reducing bacteria within the biofilm to additional anthraquinone particles, furthering the efficacy of the anthrahydroquinone treatment.

The alkali metal hydroxide solution, e.g. NaOH solution, (caustic solution) the carrier of the solubilized anthrahydroquinone, also adds to the effectiveness of the treatment by functioning as a surfactant. The caustic solution helps to disrupt the biofilm and increases the tendency for the biofilm to slough from the pipe wall. The high pH solution also shocks all of the bacteria within the biofilm, reducing all activity even in the absence of the anthrahydroquinone. Field studies in a wastewater treatment system have shown that biogenic sulfide production was mitigated with both caustic and soluble anthrahydroquinone treatments, but the maximum degree of inhibition was higher with the soluble anthrahydroquinone treatment and the restoration of the sulfide production to the original level occurred quicker with the caustic treatment.

The protocol for a treatment with soluble anthrahydroquinone salt is relatively simple. The solution typically contains active anthrahydroquinone at a concentration of about 10%. The solution is pumped from a storage tank into the pipeline transporting the water to be treated. Typically a slug dosage of solution is injected. Enough solution is injected to yield a slug in the pipeline at a concentration of about 250 ppm by wt. active anthrahydroquinone for a contact time of about 10 minutes. In some cases the slug may only need to be 50 ppm for 1 minute, while other more difficult systems to treat might require 1000 ppm for 30 minutes to control corrosion adequately. The slug dosage requirement is a function of biofilm composition, thickness, tenacity, and also the presence of hydrocarbon constituents associated with the biofilm. Velocity of the flowing water, pipe diameter and length, and the pH and buffering capacity of the water will also affect the soluble anthrahydroquinone requirements. Dispersion of the slug as it travels down the pipeline tends to reduce the pH of the slug ahead of and behind the slug. Dispersion is a function of the pipe diameter, number of bends in the pipe, and distance the slug has traveled. (Perkins, T. K. and J. A. Euchner, "Safe purging of natural gas pipelines," *SPE Production Engineering*, p. 663,1988.) The slug is injected so that dispersion is minimized and the high pH length (i.e., the bulk slug) is sufficient to give at least one minute of contact time at that high pH. High anthrahydroquinone concentrations for short contact times are typically more effective than low concentrations for long times, but circumstances may dictate that the concentration of the injected slug be limited. One such circumstance is when the water being treated contains soluble metals (especially calcium), and sufficient bicarbonate ion such that increasing the pH of the water to above about 9.5 will cause scale formation. If too high an amount of the soluble anthrahydroquinone salt in the alkali metal hydroxide solution is introduced into this water, then this will occur. In addition, the scale formation process will buffer the pH at a level which will cause anthrahydroquinone to precipitate from solution. The combined precipitate of scale and anthrahydroquinone will decrease the overall treatment effectiveness. Limiting the amount of high pH anthrahydroquinone solution injected into this water so that the final water pH is below about 9.5 will minimize the amount of scale formation while still maintaining adequate anthrahydroquinone solubility. If the pH is less than about 9.0, then no scale will form. However, significant anthrahydroquinone will precipitate due to the low pH, thereby reducing the overall effectiveness of the treatment.

The frequency of the anthrahydroquinone slug injection is based on corrosion monitoring results. Injection needs to be only frequent enough to maintain the corrosion below a predetermined level. Typically, injection is at a one-week interval, although the frequency might be as often as every other day or as infrequent as once per month. Low concentration daily injections are typically needed for short length piping systems, such as on an oil production platform, while high concentration weekly or monthly injections are typically needed for long length water transportation pipelines.

The efficacy of the treatment is increased by maintaining a pipeline pigging program. Pigging the line prior to anthrahydroquinone treatments significantly increases the anthrahydroquinone effectiveness by disturbing the biofilm, reducing its thickness, and removing solid iron sulfide deposits.

In long pipelines with numerous bends and/or in pipelines in which the flow is laminar, dispersion of the water slug containing the alkali metal salt solution of the anthrahydroquinone may become significant. This will cause anthrahydroquinone concentration in the slug to be reduced below intended levels as the leading and trailing edges of the slug mix with the flowing water. In addition, the lower pH of the water in these "tails" will result in anthrahydroquinone precipitation and possibly reduced treatment effectiveness. The leading edge "tail" can be eliminated by launching a pig into the pipeline immediately prior to beginning anthrahydroquinone solution injection. The pig will act as a barrier for mixing of the anthrahydroquinone-water slug with water even with low Reynolds Number flow and/or numerous bends in the pipeline. In addition, the pig helps to reduce the thickness of the biofilm with its scraping action, and will remove many of the iron sulfide and other solid deposits which contribute to corrosion. All of these factors will help increase the effectiveness of the anthrahydroquinone treatment. However, a pig trailing the anthrahydroquinone-water slug is detrimental to the treatment, since it would remove anthrahydroquinone which has penetrated into the biofilm.

Enhanced effectiveness of the anthrahydroquinone treatment for some applications can result from the combined utilization of anthrahydroquinone and a biocide or oxidizer. The biocide/oxidizer might be needed to reduce the amount of biofouling on a surface, which the anthrahydroquinone is responsible for long-duration inhibition of the sulfate-reducing bacteria activity. This is especially true for applications in which a biofouling problem or thick biofilm has been established prior to anthrahydroquinone treatment. Anthrahydroquinone alone will penetrate the biofilm, leaving the sulfate-reducing bacteria inactive, but other bacteria and their resultant biotic and abiotic products (especially iron sulfides) will still be present at the wall, and probably will contribute to additional corrosion. A combined anthrahydroquinone-biocide application, such as alternating materials or periodically treating with a biocide in place of an anthrahydroquinone treatment is more effective than the use of either material separately.

Anthrahydroquinone Compounds and Formulation

A wide variety of anthrahydroquinone compounds can be used in the method of the invention. As used herein, the term "anthrahydroquinone compound" refers to compounds comprising the basic tricyclic structure shown below, including 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene:

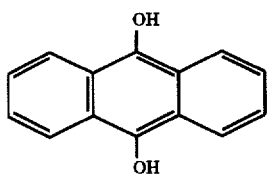

More particularly, both water-insoluble and water-soluble forms can be used. The non-ionic compounds are largely insoluble in aqueous systems, while ionic derivatives are di-alkali metal salts and are largely soluble in water. The water soluble forms are stable only in high pH anaerobic fluids. Low pH fluids (pH less than about 12) will result in the formation of the insoluble molecular anthrahydroquinone. Aerobic solutions will cause oxidation of the anthrahydroquinones to anthraquinone. Thus, anthrahydroquinones will not exist for long periods of time in an aerated environment. For these reasons, anthrahydroquinone treatments are usually implemented with the soluble ionic form in a caustic solution. NaOH solutions are preferred over other alkali metals for economic reasons.

Unlike the use of biocides for treating sulfate-reducing bacteria, the anthrahydroquinone compounds used in the invention do not kill the sulfate-reducing bacteria, but merely inhibit the corrosion activity. Interestingly enough, the active species of alkali metal salt of the anthrahydroquinone compound is believed to be water-insoluble compounds which apparently deactivate the corrosive action of the sulfate-reducing bacteria. In order for the water-insoluble compounds to be effective, they must be very finely divided to an extent that they can be dispersed into the biofilm. A lowering of the alkali metal salt solution pH will form extremely small particles of biochemically active anthrahydroquinone, which will disperse easily into the biofilm and coat the substratum.

Notwithstanding the fact that the active species seems to be the insoluble form of anthraquinone, it is nevertheless preferred to use the water-soluble anthrahydroquinone form because it diffuses into the biofilm and thus contacts the sulfate-reducing bacteria more readily. The activity of the ionic form of anthrahydroquinone seems to be derived from its conversion from the ionic (i.e., metal alkali salt) form to the non-ionic (i.e. molecular) form by which it is precipitated as very fine particles which attach to the sulfate-reducing bacteria.

Whether the soluble or insoluble anthrahydroquinone is used, it has been observed that the functional attachment of the anthrahydroquinone particles to the bacteria is limited in time by metabolism of the particles by the sulfate-reducing bacteria. Thus, application of the treating medium must be repeated periodically in order to maintain inhibition effectiveness.

The compositions are added to the medium containing the sulfate-reducing bacteria in a quantity sufficient to inhibit sulfide production. As little as 0.1 ppm by weight in the aqueous medium gives significant inhibition for many uses. In the preferred method the concentration of active anthrahydroquinone in the medium is at least 1 ppm, preferably 1–50 ppm. Greater concentrations, such as up to 1000 ppm, can be used, especially for treating pipelines of great length.

Pigging Procedure

Figure 2:
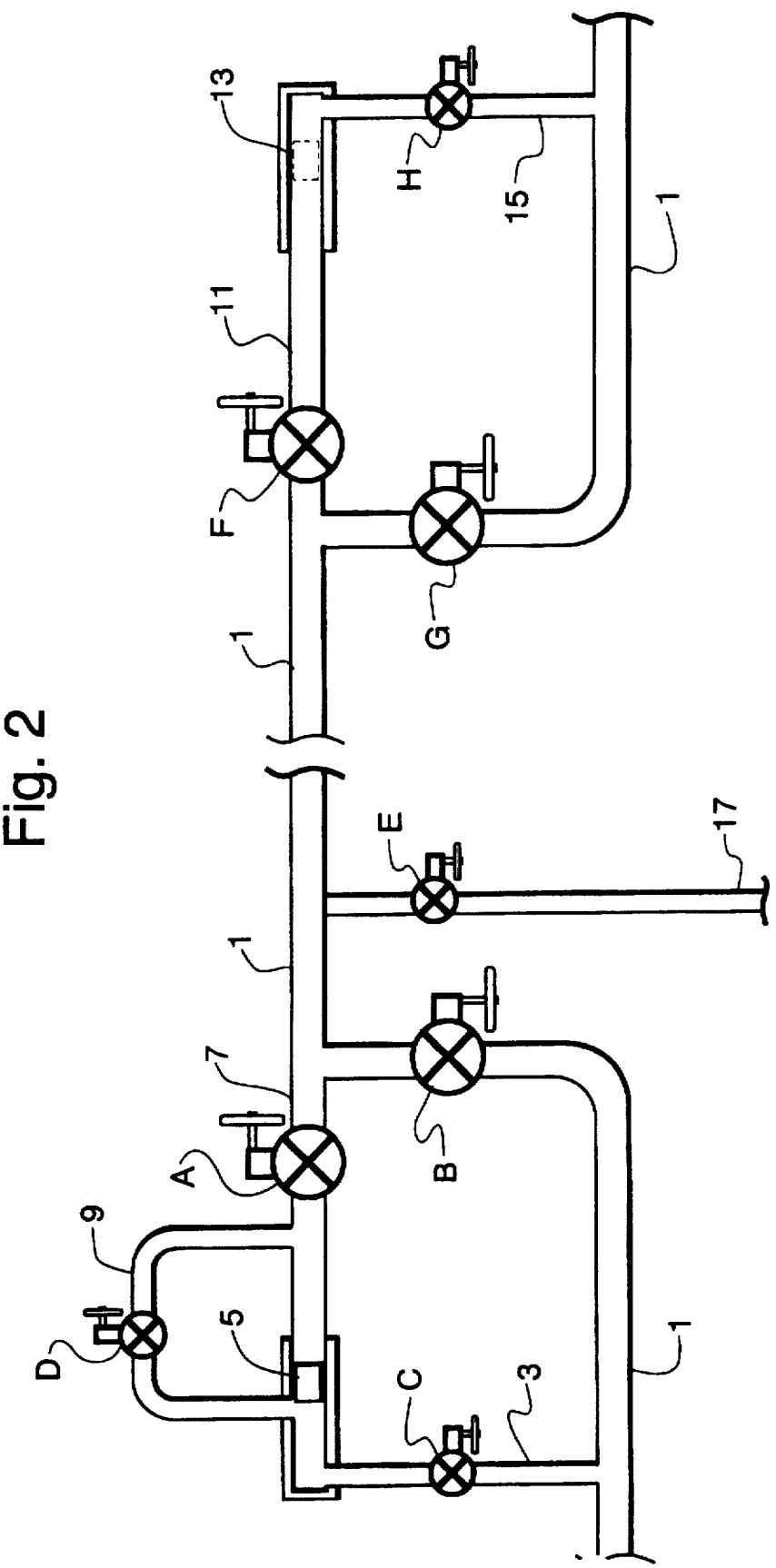

FIG. 2 is a schematic representation of a typical pipeline for transportation of liquids which has facilities for pigging (or scraping) operations. Liquid flow through the line is directed through the main pipeline 1 through upstream valve B and downstream valve G, both of which are open during normal pipeline operation. Valve C in starter line 3 and valve A in scraper outlet line 7 are closed and valve D in pressurization line 9 is open during normal pipeline operation.

When it is desired to launch the scraper (pig), valve C, which connects the main pipeline 1 with outgoing scraper barrel 5 via line 3, is opened slowly to raise the pressure in launch barrel 5 containing the scraper, to full pipeline pressure. After the launch barrel 5 has reached full pipeline pressure, valve D in pressurization line 9 is closed and scraper outlet valve A in scraper outline line 7 is opened. Then, by pinching down slowly on valve B, the differential pressure within the launch barrel rises and overcomes the friction between the scraper and the launching barrel. The scraper passes slowly through scraper outlet valve A and scraper outlet line 7 into the full flow of the main pipeline 1. After the scraper is launched, valve B is fully opened and valves A and C are closed. In addition, scraper return line valve F, main pipeline valve G and scraper receiver line valve H are opened. The scraper then proceeds through the pipeline 1, scraper return line 11 and valve F into receiving barrel 13.

As the scraper passes the juncture of inhibitor feed line 17 and the main pipeline 1, inhibitor feed valve E is opened to inject anthrahydroquinone compound into the main pipeline. Valve E is then closed as soon as the chosen quantity of anthrahydroquinone compound has been injected into the main pipeline 1.

As soon as the scraper reaches receiver barrel 13, main pipeline valve G remains fully open and valves F and H are closed. Upon venting the pressure within receiver barrel 13, it can be opened to remove the scraper.

EXAMPLE

Steel pipelines are used to transport seawater from treatment and pumping facilities to oil field water injection wells. The water is injected into specific regions of an oil-producing reservoir to provide secondary oil recovery. This provides additional oil recovery over that which results from primary, or natural, production due to the initial pressurization of the reservoir.

Treatment of the seawater prior to entering the pipeline is required to prevent corrosion of the steel pipeline and the steel tubing in the water injection wells and to improve injected water quality. The treatment process includes chlorination, filtration, deaeration, and addition of an alkali metal salt solution of anthrahydroquinone. The chlorination kills, via oxidation, the majority of the bacteria and algae entering the system with the water from the sea. The filtration removes most of the sea sediments, large particles, and biomass. Deaeration of the water is critical to remove oxygen, a key element involved in the corrosion process. Deaeration of the seawater to less than about 20 ppb oxygen essentially eliminates the potential for common oxygen-induced corrosion. Unfortunately, removing the oxygen results in an anaerobic environment, which increases the potential for anaerobic corrosion of the steel pipeline due to the activity of sulfate-reducing bacteria in the system. Addition of anthrahydroquinone is thus needed to control the activity of the corrosion-inducing sulfate-reducing bacteria.

Treatment of the seawater with soluble anthrahydroquinone is performed downstream of all other processes in the seawater treatment plant. The anthrahydroquinone solution is stored in a nitrogen-inerted (oxygen-free) feed tank connected to the suction-side of a variable-rate injection pump. This pump is connected to the pipeline with standard connecting lines and valves, on the discharge-side of the mainline seawater pumps. A flow meter indicates the volumetric rate of injection of the soluble anthraquinone. A check valve is located between the anthrahydroquinone-solution pump and the pipeline to prevent seawater from flowing back into the anthrahydroquinone-solution feed tank.

A ten-mile long, 60-inch internal diameter pipeline transports 1 million barrels of water per day from the treatment plant to an intermediate injection facility. The average seawater velocity is 3.3 ft/sec, and the flow is clearly turbulent with the Reynolds Number being $1.5 \times 10^6$.

Prior to initiating treatments in this pipeline with the alkali metal salt solution of anthrahydroquinone, significant corrosion of the steel pipeline was found to occur. Corrosion rate and presence of corrosion in the pipeline is determined by internal flush-mounted corrosion coupons, by thru-wall ultrasonic and radiographic inspections, and by various types of internally-transported 'smart' pigs. Inspection of corrosion coupons removed from the pipeline after four-months of contact with the flowing water without anthrahydroquinone treatments indicates an average corrosion rate of 5 mils per year (0.127 mm/yr.). In addition, small pits are present. The other non-destructive inspection techniques confirm that overall corrosion rate is low, but that deep pits (maximum depth up to 0.1 inch and 0.2 inch in circumference) are prevalent in certain areas of the pipeline. Both isolated pits and linked pits are found, especially on the bottom of pipeline near girth welds. These pits are characteristic of those attributed to microbially-influenced corrosion. In addition, analysis of specially internally-mounted coupons indicate the presence of about $5 \times 10^5$ sulfate-reducing bacteria cells per cm$^2$ of surface and $2 \times 10^4$ cells per cm$^2$ of other bacteria types. The presence of an ongoing corrosion process is also inferred by a high level of soluble ferrous ions and iron sulfide solids in the effluent water. 80 ppb soluble iron and no detectable solid iron sulfides are found in the influent water. However, 800 ppb soluble iron and 250 ppb equivalent iron as a solid are found in the effluent. The iron sulfide forms by the reaction of ferrous ions and sulfide ions near the surface of the pipe as the corrosion process removes ferrous ions from the steel. No sulfide is contained in the influent water. The sulfide is produced within the pipeline as a metabolic product of sulfate-reducing bacteria activity. Much of the formed iron sulfide, which is a solid, remains on the surface of the pipeline, but some is swept off by the flowing water. The total measurable iron represents a loss of 120,000 pounds of iron per year removed from the steel pipeline, or a corrosion rate of 3.6 mils per year (0.093 mm/yr.). The total sulfide associated with the solid iron sulfide in the effluent water represents 19,000 pounds of hydrogen sulfide produced per year.

A pH 13.5 anthrahydroquinone solution contains 10 wt. % active anthrahydroquinone and has a density of 10 pounds per gallon. The active anthrahydroquinone is solubilized as a metal alkali salt of anthrahydroquinone to help increase the effectiveness of transport of the active anthrahydroquinone down the pipeline and into the biofilm on the pipe wall. Soluble anthrahydroquinone solution is injected as a slug into the pipeline twice per month for thirty minutes at a rate of 36 gallons per minute, yielding a concentration of 150 ppm by weight of active anthraquinone in the thirty-minute slug of flowing seawater. The injected anthraquinone increases the seawater pH from 7.8 to 9.4 within the slug.

After four months of twice per month soluble anthrahydroquinone injections, the corrosion coupons indicate that the corrosion rate is reduced to less than 1 mil per year and pitting is minimal. Additionally, a thin tan-colored film is found adhered to the surface of the coupons, when this film is kept in an anaerobic environment, analysis shows that it is mainly anthrahydroquinone. This indicates that the injected alkali salt of the anthrahydroquinone is deposited on the coupon surface as anthrahydroquinone. Radiographic inspections of heavily corroded sites indicate that minimal corrosion has occurred since the last inspection four months previously. Total iron concentrations (solid and insoluble) in water effluent samples taken 48 hours following a treatment are 120 ppb, indicating at least a 95% reduction in iron loss from the pipe. The sulfide associated with the effluent iron sulfide particles is reduced comparably. The concentrations of both the iron and the sulfide in effluent water increases slowly with time during the semi-monthly treatment periods such that the total iron concentration at the end of the period averages about 380 ppb. Coupons removed for microbial analyses indicate that the sulfate-reducing bacteria density is $4 \times 10^4$ cell/cm$^2$ and that other bacteria are present at a level of $3 \times 10^4$ cells/cm$^2$. All of these monitoring techniques confirm that injections of soluble anthrahydroquinone into the flowing seawater effectively mitigate anaerobic microbially influenced corrosion of the steel pipeline and maintain minimal iron sulfide solids formation.

What is claimed is:

1. A non-biocidal method for inhibiting microbially influenced corrosion of microbially influenced corrosion-susceptible metal surfaces having an anaerobic biofilm containing active sulfate-reducing bacteria comprising contacting the biofilm with a liquid dispersion of an anthrahydroquinone compound selected from the group consisting of 9,10-dihydro-9,10-dihydroxyanthracene, 9,10-dihydroxyanthracene and mixtures thereof.

2. The method of claim 1 in which the anthrahydroquinone compound is in the form of solid particles having an average particle size no larger than 2.5 micrometers.

3. The method of claim 1 in which the anthrahydroquinone compound is dissolved in an aqueous solvent.

4. The method of claim 3 in which the solution of anthrahydroquinone compound has a pH of at least 12.

5. The method of claim 3 in which the anthrahydroquinone compound is the disodium salt of 9,10-dihydroxyanthracene.

6. The method of claim 1 in which the biofilm is on the surface of the metal in contact with a turbulently flowing liquid in which the anthrahydroquinone compound is dispersed.

7. The method of claim 6 in which the dispersion of anthrahydroquinone compound is introduced into liquid flowing through a pipe as a slug the volume of which is sufficient to provide liquid contact with a given point within the pipeline of at least one minute.

8. The method of claim 7, in which the solution of anthrahydroquinone compound is introduced into the pipe immediately following a pig.

9. The method of claim 6 in which an aqueous alkaline solution of the anthrahydroquinone compound is added to the flowing liquid continuously.

10. The method of claim 1 in which the biofilm is on the surface of the metal in contact with a static liquid in which the anthrahydroquinone compound is dispersed.

11. The method of claim 1 in which the microbially influenced corrosion-susceptible metal is selected from the group consisting of ferrous metals, brass, bronze and Cu/Ni alloys.

12. The method of claim 1 in which the anthrahydroquinone compound is metabolized by the sulfate-reducing bacteria.

* * * * *